US008962024B2

(12) United States Patent
Zisapel

(10) Patent No.: US 8,962,024 B2
(45) Date of Patent: Feb. 24, 2015

(54) METHOD FOR TREATING PRIMARY INSOMNIA

(75) Inventor: Nava Zisapel, Tel Aviv (IL)

(73) Assignee: Neurim Pharmaceuticals (1991) Ltd, Tel Aviv (IL)

( * ) Notice: Subject to any disclaimer, the term of this patent is extended or adjusted under 35 U.S.C. 154(b) by 2628 days.

(21) Appl. No.: 10/486,688

(22) PCT Filed: Aug. 12, 2002

(86) PCT No.: PCT/IL02/00662
§ 371 (c)(1),
(2), (4) Date: Jul. 16, 2004

(87) PCT Pub. No.: WO03/015690
PCT Pub. Date: Feb. 27, 2003

(65) Prior Publication Data
US 2004/0248966 A1 Dec. 9, 2004

(30) Foreign Application Priority Data
Aug. 14, 2001 (IL) .......................... 144900

(51) Int. Cl.
A61K 9/14 (2006.01)
A61K 31/40 (2006.01)
A61K 9/20 (2006.01)
A61K 31/4045 (2006.01)

(52) U.S. Cl.
CPC ............. *A61K 9/2027* (2013.01); *A61K 9/2009* (2013.01); *A61K 31/4045* (2013.01)
USPC .......................................... 424/486; 514/419

(58) Field of Classification Search
CPC ............ A61K 31/4045; A61K 9/2009; A61K 9/2027; A61K 9/204; A61K 31/405
USPC .......................................... 424/486; 514/419
See application file for complete search history.

(56) References Cited

U.S. PATENT DOCUMENTS

| 4,600,723 | A | * | 7/1986 | Short et al. ............... | 514/416 |
| 4,665,086 | A | | 5/1987 | Short et al. | |
| 5,403,851 | A | | 4/1995 | D—Orlando et al. | |
| 5,449,683 | A | | 9/1995 | Wurtman | |
| 5,498,423 | A | | 3/1996 | Zisapel | |
| 5,654,325 | A | | 8/1997 | Flaugh | |
| 5,688,520 | A | * | 11/1997 | Karsenty et al. ............ | 424/434 |
| 5,707,652 | A | | 1/1998 | Lewy et al. | |
| 5,776,969 | A | | 7/1998 | James | |
| 6,034,105 | A | * | 3/2000 | Mendel ..................... | 514/337 |
| 6,423,738 | B1 | | 7/2002 | Lewy et al. | |
| 6,472,421 | B1 | | 10/2002 | Wolozin | |
| 6,703,412 | B1 | | 3/2004 | Rosenthal | |

FOREIGN PATENT DOCUMENTS

| EP | 0513702 A2 | 11/1992 |
| EP | 0724878 A2 | 8/1996 |
| WO | WO 94/07487 | 4/1994 |
| WO | WO 95/03043 | 2/1995 |
| WO | WO 97/00069 | 1/1997 |

OTHER PUBLICATIONS

Zisapel, Development of a melatonin-based formulation for the treatment of insomnia in the elderly, Drug Development Research, 50: 226-234 (2000).*
Kupfer et al. (The New England Journal of Medicine, 1997, vol. 336, No. 5, pp. 341-346).*
Monti et al. ("Polysomnographic study of the effect of melatonin on sleep in elderly patients with chronic primary insomnia" Archives of Gerontology and Geriatrics 28 (1999) 85-98).*
Weibel et al. ("A single oral dose of S 22153, a melatonin antagonist, blocks the phase advancing effects of melatonin in C3H mice" Brain Research 829 (1999) 160-166).*
Dubocovich et al. ("Selective MT2 melatonin receptor antagonists block melatonin-mediated phase advances of circadian rhythm" The FASEB Journal (1998) vol. 12, 1211-1220).*
Arendt, J., et al., "Some effects of melatonin and the control of its secretion in humans," *Ciba Found Symp.*, 117:266-83 (1985) (Abstract).
Attenburrow, M.E.J., et al., "Case-control study of evening melatonin concentration in primary insomnia," *BMJ*, 312:1263-1264 (May 18, 1996).
Attenburrow, M.E.J., et al., "Low dose melatonin improves sleep in healthy middle-aged subjects," *Psychopharmacology*, 126:179-181 (1996).
Barbone, F, et al., "Association of road-traffic accidents with benzodiazepine use," *The Lancet* 352: 1331-1336 (Oct. 24, 1998).
Brusco, Luis I, et al., "Effect of Melatonin in Selected Populations of Sleep-Disturbed Patients," *Biological Signals and Receptors*, 8: 126-131 (1999).
Bubenik, George A., et al., "Prospects of the Clinical Utilization of Melatonin," *Biological Signals and Receptors*, 7: 195-219 (1998).
Costa E Silva, Jorge Alberto, et al., "Special Report from a Symposium Held by the World Health Oorganization and the World Federation of Sleep Research Societies: An Overview of Insomnia and Related Disorders—Recognition, Epidemiology and Rational Management," *Sleep*, 19(5): 412-416 (1996).
DeLaGrange, P., et al., "Therapeutic Perceptives for Melatonin Agonists and Antagonists," *Journal of Neuroendocrinology*, 15: 422-448, 2003.
Dijk, Derk-Jan, et al., "Melatonin and the Circadian Regulation of Sleep Initiation, Consolidation, Structure, and the Sleep EEG," *Journal of Biological Rhythms*, 12(6): 627-635 (Dec. 1997).
Dubocovich, M.L. et al., "Melatonin Receptors," *The IUPHAR Compendium of Receptor Characterization and Classification*, IUPHAR Media, London, pp. 187-193, (1998).

(Continued)

*Primary Examiner* — Aradhana Sasan
(74) *Attorney, Agent, or Firm* — Rothwell, Figg, Ernst & Manbeck, P.C.

(57) ABSTRACT

The invention relates to a medicament, for treating and improving the restorative quality of sleep, in a patient suffering from primary insomnia, which comprises at least one compound selected from melatonin, other melatonergic agents, melatonin agonists and melatonin antagonists, in an effective amount within the range of 0.0025 to 50 mg, and optionally one or more other therapeutically active agents.

7 Claims, No Drawings

(56) References Cited

OTHER PUBLICATIONS

Fainstein, Isidoro, et al., "Effects of Melatonin in Elderly Patients with Sleep Disturbance: A Pilot Study," *Current Therapeutic Research*, 58(12): 990-1000 (Dec. 1997).
Garfinkel, Doron, et al., "Facilitation of Benzodiazepine Discontinuation by Melatonin: A New Clinical Approach," pp. 1-22 (1997) Tel-Aviv.
Garfinkel, Doron, et al., "Facilitation of benzodiazepine discontinuation by melatonin: a new clinical approach," *Arch. Intern. Med.*, 159(20):2393-5 (Nov. 8, 1999) (Abstract).
Garfinkel, D., et al., "Improvement of sleep quality in elderly people by controlled-release melatonin," *The Lancet*, 346: 541-544 (Aug. 26, 1995).
Hahm, Huijeong, et al., "Comparison of Melatonin Products Against USP's Nutritional Supplements Standards and Other Criteria," *Journal of the American Pharmaceutical Association*, 39(1):27-31 (Jan./Feb. 1999).
Haimov, Iris, et al., "Melatonin Replacement Therapy of Elderly Insomniacs," *Sleep*, 18(7):598-603, 1995.
Haimov, Iris, et al., "Potential of Melatonin Replacement Therapy in Older Patients with Sleep Disorders," *Drugs & Aging*, 7(2):75-78 (1995).
Hays, R., et al., "Development of Brief Surveys to Assess Restorative Sleep and Daytime Consequences of Sleep," *Sleep*, 27 (Abstract Supplement: A349) (2004).
Hohagen, F., et al., "Prevalence and Treatment of Insomnia in General Practice," *Eur Arch Psychiatry Clin Neurosci*, 242: 329-336 (1993).
Jan, J.E., et al., "Clinical trials of controlled-release melatonin in children with sleep-wake cycle disorders," *J. Pineal Res.*, 29:34-39 (2000).
Lader, M. H. "Abuse Potential, Tolerance and Dependence on Chronic Anxiolytic Treatment," in *Target Receptors for Auxiolytics and Hypnotics: From Molecular Pharmacology to Therapeutics*, J. Mendlewicz, et al., eds., Int. Acad Biomed Drug Res. Basel, Karger, vol. 3, 46-54 (1992).
Lane, Elizabeth A., et al., "Pharmacokinetics of Melatonin in Man: First Pass Hepatic Metabolism," *Journal of Clinical Endocrinology Metabolism.*, 61(6): 1214-1216.
Lee, Beom-Jin, et al., "Development and Characterization of an Oral Controlled-Release Delivery System for Melatonin," *Drug Development and Industrial Pharmacy*, 22(3): 269-274 (1996).
Leipzig, Rosanne M., et al., "Drugs and Falls in Older People: A Systematic Review and Meta-analysis: I. Psychotropic Drugs," *J. Am. Geriatr. Soc*, 47(1):30-39, (Jan. 1999).
Littner, Michael, et al., "Practice Parameters for Using Polysomnography to Evaluate Insomnia: An Update," *Sleep*, 26(6): 754-760 (2003).
Millet, Bruno, et al., "Prospects for anxiolytic therapy: a reflection from different viewpoints," *Drug Discovery Today*, 3(10): 471-479 (Oct. 1998).
Mintzer, Miriam Z. et al., Selective effects of zolpidem on human memory functions, *J. of Psychopharmacology*, 13(1): 18-31 (1999).
Monti, J.M., et al., "Polysomnographic study of the effect of melatonin on sleep in elderly patients with chronic primary insomnia," *Archives of Gerontology and Geriatrics*, 28:85-98, (1999).
Morin, Charles M. "Measuring outcomes in randomized clinical trials of insomnia treatments," *Sleep Medicine Reviews*, 7(3):263-279 (2003).
Morin, Charles M., et al., "Behavioral and Pharmacological Therapies for a Late-Life Insomnia, A Randomized Controlled Trial," *Jama*, 281(11): 991-999 (Mar. 17, 1999).
Ohayon, Maurice M., "Prevalence and Correlates fo Nonrestorative Sleep Complaints," *Arch Intern Med*, 165: 35-41 (Jan. 10, 2005).
Parrino, Liborio., et al., "Polysomnographic effects of hypnotic drugs. A review," *Psychopharmacology*, 126: 1-16 (1996).
Perlis, M.L., et al., Psychophysiological insomnia: the behavioural model and a neurocognitive perspective, *J. Sleep Res*, 6(3): 179-188 (1997).
Riemann, Dieter, et al., "The Guidelines for 'Non-Restorative Sleep': Relevance for the Diagnosis and Therapy of Insomnia," *Somnologie*, 7: 66-76 (2003).
Roth, T., et al., "Consensus for the Pharmacological Management of Insomnia in the New Millenium," *International Journal of Clinical Practice*, 55(1): 1-10 (Jan./Feb. 2001).
Rush, Craig.R., "Behavioral Pharmacology of Zolpidem Relative to Benzodiazepines: A Review," *Pharmacology Biochemistry and Behavior*, 61(3): 253-69 (1998).
Shader, Richard I, et al., "Use of Benzodiazepines in Anxiety Disorders," *N. Engl. J. Med.*, 328(19): 1398-405 (May 13, 1993).
Turek, Fred W., et al., "Melatonin, sleep, and circadian rhythms: rationale for development of specific melatonin agonists," *Sleep Medicine*, 5: 523-532 (2004).
Uchikawa, Osamu., et al., "Synthesis of a Novel Series of Tricyclic Indan Derivatives as Melatonin Receptor Agonists," *J. Med. Chem.*, 45(19): 4222-4239 (2002).
Walach, Harold., "Placebo and placebo effects—a concise review," *Focus on Alternataive and Complementary Therapies*, 8(2): 178-187 (2003).
Witt-Enderby, P.A., et al., "Melatonin receptors and ligands," *Vitam. Horm.*, 58:321-54 (2000) (Abstract).
Zhdanova, Irina V., et al., "Melatonin: A Sleep-Promoting Hormone," *Sleep*, 20(10):899-907 (1997).
Zhdanova, Irina V., et al., "Sleep-inducing effects of low doses of melatonin ingested in the evening," *Clinical Pharmacology & Therapeutics*, 57(5):552-558 (May 1995).
Zisapel, Nava, et al., "Effects of Fast-And Controlled-Release Melatonin Formulations on Daytime Sleep and Mood," *Pineal Update*, pp. 355-360 (1997) PJD Publications Limited, Westbury, NY.
Zisapel, Nava, "The Use of Melatonin for the Treatment of Insomnia," *Biological Signals and Receptors*, 8:84-89 (1999).
Bonnet, M.H. et al., "Physiological Activation in Patients with Sleep State Misperception," Psychosomatic Medicine, 59(5): 533-540 (Sep.-Oct. 1997).
Shah, Jaymin, et al., "Feasibility and Functionality of OROS® Melatonin in Healthy Subjects," Journal of Clinical Pharmacology, 39:606-612 (1999).
Ellis, C.M., et al., "Melatonin and insomnia," J. Sleep Res., 1996, pp. 61-65, vol. 5. European Sleep Research Society.
Hughes, Rod J., et al., "The Role of Melatonin and Circadian Phase in Age-related Sleep-maintenance Insomnia: Assessment in a Clinical Trial of Melatonin Replacement," Sleep, 1998, pp. 52-68, vol. 21, No. 1.
James, Steven P., et al., "Melatonin Administration in Insomnia," Neuropsychopharmacology, 1989, pp. 19-23, vol. 3, No. 1. Elsevier Science Publishing Co., Inc., New York, NY.
MacFarlane, James G. et al., "The Effects of Exogenous Melatonin on the Total Sleep Time and Daytime Alertness of Chronic Insomniacs: A Preliminary Study," Biol. Psychiatry, 1991, pp. 371-376, vol. 30.
Jean-Louis, G., et al., "Melatonin effects on sleep, mood, and cognition in elderly with mild cognitive impairment," Journal of Pineal Research, 25:177-183 (1998).
Roth, Thomas et al., "Nonrestorative Sleep as a Distinct Component of Insomnia," Sleep, 33(4):449-458 (2010).
Annex I Summary of Product Characteristics, p. 2, Section 4.1 Therapeutic Indications from the European Medicine Evaluation Agency (EMEA) website listing for this drug (2010).
Rozerem "Full Prescribing Information", 2005-2010, 18 pages.
EMA "Circadin melatonin" European Medicines Agency, Science Medicines Health, 2010, 3 pages.

\* cited by examiner

METHOD FOR TREATING PRIMARY INSOMNIA

FIELD OF THE INVENTION

The present invention relates to a method for treating primary insomnia (as defined by DSM-IV or nonorganic insomnia as defined by ICD-10) when characterized by non-restorative sleep, to the use of melatonin or certain other compounds in the manufacture of a medicament for this purpose, and to a medicament comprising a combination of compounds, for use in improving both the quality and quantity of sleep, in primary insomnia.

BACKGROUND OF THE INVENTION

Sleep disorders, which are complex, are widespread, especially in Western industrial countries, in which it is estimated that about one third of the adult population reports at least occasional difficulties with sleeping, while at least half of the sleep-disordered population have had sleep complaints for years. In U.S. Pat. No. 5,776,969 (James), which discloses a method of treating various sleep disorders, by therapy with a specified combination of chemical compounds, there is discussed and defined inter alia, primary insomnia, which may or may not be characterized by non-restorative sleep.

The definition of primary insomnia in the fourth revision of the Diagnostic and Statistical Manual of Mental Disorders (DSM-IV) (American Psychiatric Association, 1994) states: "The predominant complaint is difficulty initiating or maintaining sleep, or non-restorative sleep, for at least one month. The sleep disturbance (or associated daytime fatigue) causes clinically significant distress or impairment in social, occupational or other important areas of functioning." Furthermore, according to the definition, non-restorative sleep alone is sufficient to establish the diagnosis of primary insomnia, providing it results in impaired daytime functioning.

The tenth revision of the International Classification of Diseases (ICD-10) (World Health Organisation, 1991) describes nonorganic insomnia as "a condition of unsatisfactory quantity and/or quality of sleep." It goes on to state that "there are people who suffer immensely from the poor quality of their sleep, while sleep in quantity is judged subjectively and/or objectively as within the normal limits."

The diagnostic guidelines from ICD-10 state that the essential clinical features for a definitive diagnosis of primary insomnia are as follows: a) the complaint is either of difficulty falling asleep or maintaining sleep, or of poor quality sleep; b) the sleep disturbance has occurred at least three times per week for at least one month; c) there is preoccupation with the sleeplessness and excessive concern over its consequences at night and during the day; d) the unsatisfactory quantity and/or quality of sleep either causes marked distress or interferes with social and occupational functioning. Thus, there is repeated emphasis in ICD-10 on the equal importance of quality of sleep and quantity of sleep in the diagnosis of insomnia. The invention thus relates to primary insomnia (DSM-IV) or nonorganic insomnia (ICD-10).

Because, in normal humans, the natural hormone melatonin has an increased nocturnal concentration in the blood (according to a particular profile, see e.g. U.S. Pat. No. 5,498,423 (Zisapel)), compared with its daytime concentration, and because also a lack of nocturnal melatonin appears to correlate with the existence of sleep disorders, especially although not exclusively in the elderly, the possibility of administering exogenous melatonin to ameliorate sleep disorders has been investigated and is the subject of many scientific papers.

Thus, for example, in James, S. P., et al. (Neuropsychopharmacology 1990, 3:19-23), melatonin (1 and 5 mg) and placebo were given at 10:45 pm for one night each to 10 polysomnographically pre-screened insomniacs with a mean age of 33.4 years. These patients (who may not necessarily have had non-restorative sleep related insomnia) had quantitative sleep deficits that were demonstrable by PSG. Administration of melatonin did not alter sleep latency, sleep efficiency, total sleep time, or wake after sleep onset. The patients reported improved sleep quality, though they were not more rested in the morning and believed that their total sleep time had been shorter when on melatonin.

In Ellis, C. M., et al. (J. Sleep Res., 1996, 5: 61-65), where melatonin (5 mg) was given at 8:00 pm for 1 week to patients with psychophysiological insomnia, there was no reported change in sleep quantity or quality; 8 patients out of 15 were unable to distinguish the period of active melatonin treatment.

In Hughes, R. J., et al. (Sleep 1998, 21: 52-68), immediate release and controlled release formulations of melatonin (0.5 and 5 mg) were given 30 min before sleep and additionally, an immediate release preparation of 0.5 mg melatonin was given halfway through the night to polysomnographically pre-screened elderly patients with sleep maintenance insomnia. They found that both melatonin preparations reduced sleep latency but did not alter wake time after sleep onset (an important variable in sleep maintenance insomnia) or total sleep time. No melatonin-induced changes in reported sleep quality or daytime measure of mood and alertness were found.

MacFarlane J. G., et al. (Biol Psychiatry 1991, 30(4): 371-6) have reported that melatonin (75 mg per os), administered at 10 PM daily to 13 insomniac patients for 14 consecutive days gave a significant increase in the subjective assessment of total sleep time and daytime alertness, whereas 7/13 patients reported no significant effect on subjective feelings of well-being.

Thus, there appears to be little or no evidence from published articles, that administration of exogenous melatonin (or other melatonergic agents, melatonin agonists or melatonin antagonists), in the dosages contemplated by the present invention, would be likely to improve the restorative quality of sleep in subjects affected by primary insomnia characterized by non-restorative sleep.

However, in contrast with the results of the above published papers, the present inventors have surprisingly found that melatonin (and other melatonergic agents, melatonin agonists or melatonin antagonists) in fact improves the restorative quality of sleep in subjects suffering from primary insomnia. Suitable melatonin agonists and antagonists for use in the present invention include (but are not restricted to) such compounds described in U.S. Pat. No. 5,151,446; U.S. Pat. No. 5,318,994; U.S. Pat. No. 5,385,944; U.S. Pat. No. 5,403,851; and International Patent Specification No. WO 97/00069.

The entire contents of the above-mentioned US Patents and literature references are incorporated herein by reference.

SUMMARY OF THE INVENTION

The present invention provides in one aspect, use of at least one compound selected from melatonin, other melatonergic agents, melatonin agonists and melatonin antagonists in an effective amount within the range of 0.0025 to 50 mg, in the manufacture of a medicament, for treating and improving the restorative quality of sleep, in a patient suffering from primary insomnia, wherein the medicament comprises also at least one pharmaceutically acceptable diluent, preservative, antioxidant, solubilizer, emulsifiers adjuvant or carrier.

In another aspect, the invention provides a method for treating and improving the restorative quality of sleep, in a patient suffering from primary insomnia, which comprises administering an effective amount of at least one compound selected from melatonin, other melatonergic agents, melatonin agonists and melatonin antagonists, to said patient, said effective amount being within the range of 0.0025 to 50 mg.

In still another aspect, the invention provides a medicament, for use in improving both the quality and quantity of sleep, in primary insomnia, which comprises at least one compound selected from melatonin, other melatonergic agents, melatonin agonists and melatonin antagonists, and at least one additional therapeutic agent selected from anxiolytics, antidepressants, hypnotics, sedatives, antihypertensives, analgesics, dopaminergic agonists, antipsychotics, minor tranquilizers, anorectics and anti-inflammatory drugs, in addition to at least one pharmaceutically acceptable diluent, preservative, antioxidant, solubilizer, emulsifiers adjuvant or carrier.

DETAILED DESCRIPTION OF THE INVENTION

The medicament of, or useful in the invention is preferably further characterized by at least one of the following features:
(i) it is adapted for oral, rectal, parenteral, transbuccal, intrapulmonary (e.g. by inhalation) or transdermal administration;
(ii) it is in unit dosage form, each unit dosage comprising an amount of said at least one compound which lies within the range of 0.025-10 mg;
(iii) it is a prolonged release formulation;
(iv) it is in a depot form which will release the said at least one compound slowly in the body, over a preselected time period;
(v) it comprises also at least one additional therapeutic agent selected from anxiolytics, antidepressants, hypnotics, sedatives, antihypertensives, analgesics, dopaminergic agonists, antipsychotics, minor tranquilizers, anorectics and anti-inflammatory drugs.

In the medicament provided by the invention, the at least one compound is preferably present in an amount effective in improving the restorative quality of sleep, in a patient suffering from primary insomnia (as defined above), and the at least one additional therapeutic agent is preferably present in an amount effective in improving the quantity of sleep in the patient.

In the method of the invention for treating and improving the restorative quality of sleep, in a patient suffering from primary insomnia (as defined above) an effective amount of at least one compound selected from melatonin, other melatonergic agents, melatonin agonists and melatonin antagonists, is preferably administered in the form of a medicament, which comprises also at least one pharmaceutically acceptable diluent, preservative, antioxidant, solubilizer, emulsifiers adjuvant or carrier. More preferably, the medicament is further characterized by at least one of the features (i), (ii), (iii) and (iv), set forth above.

In the medicament with which the present invention is concerned, the pharmaceutically acceptable diluents, preservatives, solubilizers, emulsifiers, adjuvants and carriers are those conventionally used in pharmaceutical formulations.

For oral administration, the medicament may be utilized as e.g. tablets, capsules, emulsions, solutions, syrups or suspensions. For parenteral administration, the medicament may be utilized in the form of ampoules, or otherwise as suspensions, solutions or emulsions in aqueous or oily vehicles. The need for suspending, stabilizing and/or dispersing agents will of course take account of the fact of the solubility or otherwise of the active compounds, in the vehicles which are used in particular embodiments. The medicament may additionally contain e.g. physiologically compatible preservatives and antioxidants.

The medicament may also be utilized as suppositories with conventional suppository bases such as cocoa butter or other glycerides.

As described above, the at least one compound selected from melatonin, other melatonergic agents, melatonin agonists and melatonin antagonists, may be administered in conjunction with (i.e. simultaneously, separately or sequentially) other compounds which are known in the art to be useful for enhancing sleep quantity, including e.g., at least one additional therapeutic agent selected from anxiolytics, antidepressants, hypnotics (benzodiazepines as well as non-benzodiazepines), sedatives, antihypertensives, analgesics, dopaminergic agonists, antipsychotics, minor tranquilizers, anorectics and anti-inflammatory drugs. Examples of such additional therapeutic agents are adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, zopiclone and salts thereof, and combinations thereof.

Suitable classes of antidepressants include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, alpha-adrenoreceptor antagonists and atypical anti-depressants. Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof. Suitable selective serotonin reuptake inhibitors include: fluoxetine, fluvoxamine, paroxetine and sertraline, and pharmaceutically acceptable salts thereof. Suitable monoamine oxidase inhibitors include: isocarboxazid, phenelzine, tranylcypromine and selegiline, and pharmaceutically acceptable salts thereof. Suitable reversible inhibitors of monoamine oxidase include: moclobemide, and pharmaceutically acceptable salts thereof. Suitable serotonin and noradrenaline reuptake inhibitors of use in the present invention include: venlafaxine, and pharmaceutically acceptable salts thereof. Suitable CRF antagonists include those compounds described in International Patent Specifications Nos. WO 94/13643, WO 94/13644, WO 94/13661, WO 94113676 and WO 94/13677 (the entire contents of which are incorporated herein by reference). Suitable atypical anti-depressants include: bupropion, lithium, nefazodone, trazodone and viloxazine, and pharmaceutically acceptable salts thereof. Suitable classes of anxiolytics include benzodiazepines and 5-HT1A agonists or antagonists, especially 5-HT1A partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable 5-HT1A receptor agonists or antagonists include, in particular, the 5-HT1A receptor partial agonists buspirone, flesinoxan, gepirone and ipsapirone, and pharmaceutically acceptable salts thereof.

The additional therapeutic agent may be e.g., an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712, the entire contents of these US Patents being incorporated herein by reference. Desamethasone (Decadron™) is particularly preferred.

The at least one compound selected from melatonin, other melatonergic agents, melatonin agonists and/or antagonists, may be administered in conjunction with the use of physical methods such as with light therapy or electrical stimulation, e.g. scheduling bright light administration, ordinary-intensity light exposure, or exposure to dim-light or darkness. In one embodiment of the present invention, administration may be accompanied by having a subject wear dark or red goggles at the time of administration to provide additive effects of the treatment plus darkness. In another embodiment, an additional therapeutic agent may be an anorectic agent for the treatment or prevention of eating disorder, such as bulimia nervosa or bulimia that may impair quantity of sleep. Suitable anorectic agents are, e.g., aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine. Particularly preferred anorectic agents include amphetamine and derivatives thereof such as amphetamine, benzphetamine, chlorphentermine, clobenzorex, cloforex, clortermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine. A particularly suitable class of anorectic agent are the halogenated amphetamine derivatives, including chlorphentermine, cloforex, clortermine, dexfenfluramine, fenfluramine, picilorex and sibutramine. Particularly preferred halogenated amphetamine derivatives of use in combination with a compound of the present invention include: fenfluramine and dexfenfluramine. It will be appreciated that for the ancillary treatment or prevention of obesity, the compounds of the present invention may also be used in combination with a selective serotonin reuptake inhibitor (SSRI). Suitable selective serotonin reuptake inhibitors include: fluoxetine, fluvoxamine, paroxetine and sertraline. Pharmaceutically acceptable salts of all of these compounds, where applicable, are of course included.

The invention will be illustrated by the following Examples.

EXAMPLE I

Method.

The effect of a prolonged-release formulation of melatonin on sleep quantity and quality in 40 elderly primary insomnia patients (aged 76 [SD 8] years) were studied in a randomized, double-blind, two parallel group study. The subjects were treated for 3 weeks every evening with melatonin (2 mg prolonged-release formulation) or placebo. Full-night polysomnographic recordings were performed on the last two days of treatment to measure quantitative aspects of sleep. On each morning following sleep recording in the laboratory, a battery of psychomotor tests was taken by all patients to assess daytime vigilance. In addition, patients recorded every day in diaries their perceived quality of sleep the previous night.

Results.

Sleep induction (as measured by sleep onset latency (SL), duration of wake prior sleep onset (DWAPSO) and % of time spent asleep prior to sleep onset (DWAPSOP) significantly improved with melatonin compared to placebo: SL time was shortened by 9 min on average ($P=0.011$), (DWAPSO) and DWAPSOP also improved significantly: ($p=0.011$, and $p=0.02$ respectively). For the sleep maintenance variables (number of awakenings, duration of wake after sleep onset (DWASO), sleep efficiency, total sleep time) there were no differences between melatonin and placebo. There were no differences between groups in sleep architecture or all night EEG spectral analysis.

Conclusions.

These results show beneficial effects of melatonin on sleep initiation, similar to effects of hypnotic drugs. The hypnotic effects of melatonin were in line with reports in the literature showing that melatonin promotes sleep in humans without altering normal sleep architecture. In contrast to this apparently hypnotic effect, psychomotor skills were significantly higher in the melatonin compared to placebo-treated group: significant treatment effects for the Critical Flicker fusion test and total reaction time under melatonin vs. placebo were observed at the end of treatment.

These results thus show for the first time the association of hypnotic effect (shortening of sleep latency) by melatonin with enhanced daytime vigilance in primary insomnia patients suggesting that the restorative value of sleep has increased in these patients. With hypnotic drugs shortening of sleep latency and improved quality of sleep is associated with impaired psychomotor skills in the morning or at best no significant deterioration. No hypnotic drug has ever been shown to increase daytime vigilance. Surprisingly, in their diaries, patients did not evaluate the ease of getting to sleep as being better with melatonin compared to placebo. In fact, the patients judged their quality of sleep to be improved with melatonin but not placebo treatment. The restorative value of sleep may thus be associated with a perceived improvement in quality of sleep.

EXAMPLE 2

Method.

The effect of a prolonged-release formulation of melatonin on subjectively assessed sleep quality and daytime vigilance in 170 elderly primary insomnia patients (aged 68.5 [SD 8.3] years) were studied in a randomized, double-blind, two parallel group study. The subjects were treated for 2 weeks with placebo to establish baseline characteristics and then for 3 weeks with melatonin (2 mg per night of prolonged-release formulation) or placebo. On the last three days of the baseline and treatment periods patients were asked to assess the quality of their sleep the previous night and their feeling in the morning. The quality of sleep question was "How would you compare the quality of sleep using the medication with non-medicated (your usual) sleep?" The patients marked the level of their perceived quality of sleep on a 100 mm, non-hatched horizontal line with two endpoints. The left endpoint was labeled "more restless than usual" and the right endpoint was labeled "more restful than usual". The waking state question was "How do you feel now?" The patients marked the level of their perceived waking state on a 100 mm, non-hatched horizontal line with two endpoints. The left endpoint was labeled "tired" and the right endpoint was labeled "alert". The distance of the patient mark from the right endpoint in mm was measured (a reduction in value therefore indicates a better sleep or less tired state). The mean distance across the three nights was calculated.

Results.

It was found that both quality of sleep and daytime alertness significantly improved with melatonin compared to placebo (Table 1) showing a link between improved restful sleep and less fatigue in the morning.

TABLE 1

Effects of melatonin and placebo on subjectively assessed quality of sleep and daytime alertness in primary insomnia patients.

| Response | Melatonin, change in mm mean (SE) | Placebo, change in mm mean (SE) |
|---|---|---|
| Change in perceived quality of sleep | −24.3 (2.6)* | −17.6 (2.1) |
| Change in perceived daytime alertness | −16.8 (2.7)* | −6.6 (2.0) |

*The difference from placebo is significant ($p < 0.05$).

Conclusions.

These results show that melatonin enhanced the restorative value of sleep in these primary insomnia patients.

EXAMPLE 3

Method.

The effect of melatonin on subjectively assessed sleep quality and daytime vigilance in 131 primary insomnia patients (aged 20-80 years) were studied in a randomised, double-blind, parallel group study. The subjects were treated for 1 week with placebo to establish baseline characteristics and then for 3 weeks with melatonin (2 mg per night of prolonged-release formulation) or placebo. On the last three days of the baseline and treatment periods patients were asked to assess the quality of their sleep the previous night and their feeling at daytime as described in Example 2.

Results.

In the 55 years and older patients, there was an improvement of quality of sleep and daytime alertness as found in the other studies in the elderly (see Example 2). Surprisingly, it was found that in patients <55 years of age there was a significant worsening of the quality of sleep and daytime alertness compared to placebo. The results are tabulated in Table 2.

TABLE 2

Effects of melatonin and placebo on subjectively assessed quality of sleep and daytime alertness in primary insomnia patients aged 55 and higher and patients aged less than 55 years (mean in mm (SE)).

| Response | Melatonin | Placebo |
|---|---|---|
| Change in perceived quality of sleep Patients aged 55 and over | −13.1 (4) | −7.4 (3) |
| Change in perceived daytime alertness Patients aged 55 and over | −16.3 (3.7) | −7.5 (3.3) |
| Change in perceived quality of sleep Patients aged less than 55 | −1.6 (2) | −13.7 (5) |
| Change in perceived daytime alertness Patients aged less than 55 | | −4.0 (4) |

Conclusions.

The elderly are more likely to have maintenance and non-restorative sleep problems, as 40% of older individuals complain about sleep problems, including disturbed or "light" sleep, and undesired daytime sleepiness (Vitiello, Michael Geriatrics Vol. 54(11):47-52 1999). Younger people typically have sleep onset problems (Roth, Thomas and Roehrs, Timothy Sleep Vol 19(8): S48-49 1996), and their main problem may be due to sleep deficit not non-restorative sleep. These results (Table 2) clearly indicate that melatonin was effective in primary insomnia related to non-restorative sleep, but can be detrimental to insomnia related to other aetiologies (e.g. sleep deficit due to inability to initiate sleep).

EXAMPLE 4

Method.

The effect of melatonin (2 mg prolonged-release formulation), N, N, 6-trimethyl-2-p-tolylimidazo[1,2-a]pyridine-3-acetamide (zolpidem; 10 mg) and placebo on psychomotor skills and driving performance were assessed in 16 healthy elderly volunteers age 59.4 years (SD 3.2). In a randomized, double-blind, crossover study the subjects were given a tablet of placebo in the evening to establish baseline and then a tablet of melatonin, zolpidem or placebo in a random order in the evening with one week with no treatment in between treatments. A battery of psychomotor tasks, driving performance and wake EEG during a driving test were studied in the patients at pre-selected intervals after the administration of the tablet.

Results.

There were several acute impairments seen with zolpidem compared to placebo, which were resolved by 12.5 hours post-dosing. The effects found with zolpidem were seen across measures of attention, episodic secondary memory and motor coordination. Memory efficiency decreased with zolpidem 10 mg for both recalls (immediate and delayed) compared to placebo and melatonin 2 mg. No cognitive effect of melatonin, adverse or otherwise was identified. For the driving performance, significant differences were noticed with zolpidem 10 mg for the standard deviations of the parameters (absolute speed, deviation from the speed limit and deviation from the ideal route), and the number of collisions. Indeed, the standard deviations for the absolute speed and the deviations from the speed limit and ideal route parameters were increased 2 hours post-dosing with zolpidem 10 mg. These standard deviation increases suggest that driving was irregular, fluctuating not only for the speed but also for the road holding. The variations observed for the ideal route parameter corroborated the increased number of collisions counted 2 hours post-dosing, in the Zolpidem 10 mg group. No such effects were seen with melatonin (prolonged release 2 mg formulation).

Conclusions.

These studies show that improvement in quality of sleep reported by patients (as is the case with zolpidem) does not necessarily indicate enhanced restorative sleep, since it is not associated with improved daytime vigilance. More generally, this Example demonstrates that melatonin does not improve vigilance in non-insomnia patients.

EXAMPLE 5

Preparation of Prolonged Release Melatonin Formulation

The prolonged release oral dosage formulation used in Examples 1-4 was prepared by direct compression with ground powder mass of an acrylic resin Eudragit (Rohm Pharma). Melatonin (2 mg; Sygena, Switzerland) was mixed with 40 mg of calcium hydrogen phosphate and 80 mg lactose in the dry state into the ground table mass (40 mg Eudragit RSPO) and the mixture was compressed at 2.5 tons in a cylindrical punch 7 mm diameter.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The invention claimed is:

1. Method for treating and improving the restorative quality of sleep in a patient suffering from non-restorative sleep as an element of primary insomnia, which comprises administering an effective amount of at least one compound selected from the group consisting of melatonin, other melatonergic agents, melatonin agonists and melatonin antagonists, to said patient, said effective amount being within the range of 0.0025 to 50 mg, wherein said at least one compound selected from the group consisting of melatonin, other melatonergic agents, melatonin agonists and melatonin antagonists is the only therapeutically active agent administered according to said method.

2. Method according to claim 1, wherein the melatonin is administered in the form of a medicament, which comprises also at least one pharmaceutically acceptable diluent, preservative, antioxidant, solubilizer, emulsifiers, adjuvant or carrier.

3. Method according to claim 2, wherein the medicament is further characterized by at least one of the following features:
  (i) it is adapted for oral, rectal, parenteral, transbuccal, intrapulmonary (e.g. by inhalation) or transdermal administration;
  (ii) it is in unit dosage form, each unit dosage comprising an amount of said at least one compound which lies within the range of 0.025-10 mg;
  (iii) it is a prolonged release formulation;
  (iv) it is in a depot form which will release said at least one compound slowly in the body, over a preselected time period.

4. Method according to claim 3, wherein said prolonged release formulation includes an acrylic resin.

5. The method of claim 1, which comprises administering a prolonged release formulation containing as the sole therapeutically active ingredient an effective amount of at least one compound selected from the group consisting of melatonin, other melatonergic agents, melatonin agonists and melatonin antagonists.

6. The method of claim 1, wherein said method consists of said administering step.

7. The method of claim 1, wherein said method consists of administering an effective amount of melatonin.

* * * * *